(12) United States Patent
Hubbell et al.

(10) Patent No.: US 7,029,688 B2
(45) Date of Patent: Apr. 18, 2006

(54) METHODS AND COMPOSITIONS TO PREVENT FORMATION OF ADHESIONS IN BIOLOGICAL TISSUES

(75) Inventors: Jeffrey A. Hubbell, Zurich (CH); Natalie D. Winblade, Seattle, WA (US); Donald L. Elbert, St. Louis, MO (US)

(73) Assignee: California Institute of Technology, Pasadena, CA (US)

( * ) Notice: Subject to any disclaimer, the term of this patent is extended or adjusted under 35 U.S.C. 154(b) by 399 days.

(21) Appl. No.: 10/403,344

(22) Filed: Mar. 28, 2003

(65) Prior Publication Data

US 2003/0185787 A1 Oct. 2, 2003

Related U.S. Application Data

(62) Division of application No. 09/140,781, filed on Aug. 27, 1998, now Pat. No. 6,596,267.

(60) Provisional application No. 60/056,854, filed on Aug. 27, 1997.

(51) Int. Cl.
| | |
|---|---|
| *A61P 2/02* | (2006.01) |
| *A61P 17/02* | (2006.01) |
| *A61P 29/00* | (2006.01) |
| *A61P 35/00* | (2006.01) |
| *A61K 47/30* | (2006.01) |

(52) U.S. Cl. .................. 424/422; 424/423; 514/772.1; 427/2.12; 427/2.24; 427/2.28

(58) Field of Classification Search .......... 424/422–23; 514/772.1; 427/2.12, 2.24, 2.28
See application file for complete search history.

(56) References Cited

U.S. PATENT DOCUMENTS

| | | | |
|---|---|---|---|
| 4,111,863 | A | 9/1978 | Wulff et al. |
| 4,409,391 | A | 10/1983 | Broadhurst et al. |
| 4,886,924 | A | 12/1989 | Goralski et al. |
| 5,240,602 | A | 8/1993 | Hammen et al. |
| 5,312,959 | A | 5/1994 | Sieja et al. |
| 5,578,442 | A | 11/1996 | Desai et al. |
| 5,594,042 | A | 1/1997 | Glover et al. |
| 5,624,762 | A | 4/1997 | Glover et al. |
| 5,644,019 | A | 7/1997 | Po' et al. |
| 5,691,292 | A | 11/1997 | Marshall et al. |
| 5,908,624 | A | 6/1999 | Scott et al. |
| 6,129,912 | A | 10/2000 | Hortin et al. |
| 6,312,685 | B1 | 11/2001 | Fisher et al. |

FOREIGN PATENT DOCUMENTS

WO    WO 97/28254    8/1997

OTHER PUBLICATIONS

Adamyan, et al., "Use of fibrin glue in obstetrics and gynecology: a review of the literature," Int. J. Fertil. 36: 76-88 (1991).

Aoki, et al., "Endothelial cell differentiation into capillary structures by copolymer surfaces with phenylboronic acid groups," J. Biomater. Sci. 7: 539-550 (1995).

Apple, et al., "Posterior capsule opacification," Survey Ophthalmol. 37: 73-116 (1992).

Burns, et al., "A hyaluronate based gel for the prevention of postsurgical adhesions: evaluation in two animal species," Fertility and Sterility 66(5): 814-821 (1996).

Claesson, et al., "Direct measurements of steric interactions between mica surfaces covered with electrostatically bound low-molecular-weight polyethylene oxide," J. Colloid Interface Sci. 117: 366-374 (1986).

De Iaco, et al., "Fibrin sealant in laparoscopic adhesion prevention in the rabbit uterine horn model," Fertility and Sterility 62: 400-404 (1994).

Desai, et al., "Tissue response to intraperitoneal implants of polyethylene oxide-modified polyethylene terephthalate," Biomaterials 13: 505-510 (1992).

Dizerega, "Contemporary adhesion prevention" Fertility and Sterility 61: 219-235 (1994).

Dunn, et al,. "Polystyrene-poly (ethylene glycol) (PS-PEG2000) particles as model systems for site specific drug delivery. 2. The effect of PEG surface density on the in vitro cell interaction and in vitro biodistribution," Pharm. Res. 11: 1016-1022 (1994).

Elbert, et al., "Self-assembly and steric stabilization at heteroegnous, biological surfaces using absorbing block copolymers," Chemistry and Biology 5: 177-183 (1998).

(Continued)

*Primary Examiner*—Edward J. Webman
(74) *Attorney, Agent, or Firm*—Pabst Patent Group LLP

(57) ABSTRACT

The invention discloses materials that adsorb readily to the surfaces of body tissues in situ and provide a steric barrier between such tissues, so that tissue adhesions, which typically form following surgical procedures, are minimized. These materials contain a polymer of hydrophilic molecules such as polyethylene glycol (PEG) bound to a polymer that spontaneously adsorbs to biological tissue such as phenylboronic acid (PBA). The PEG-PBA co-polymer can be formed in a variety of geometries. The materials can also be used to coat prosthetics and other implants.

23 Claims, No Drawings

OTHER PUBLICATIONS

Elbert, et al., "Reduction of fibrous adhesion formation by a copolymer possessing an affinity for anionic surfaces," J. Biomed. Mater. Res. 42(1): 55-65 (1998).

Hanahan, "Signaling vascular morphogenesis and maintenance," Science 277: 48-60 (1997).

Holtz, "Prevention and management of peritoneal adhesions," Fertility and Sterility 41: 497-507 (1984).

Hubbell, et al., "Endothelial cell-selective materials for tissue engineering in the vascular graft via a new receptor" Bio/Technology 9: 568-572 (1991).

James, et al., "A saccharide 'sponge.' Synthesis and properties of a dendritic boronic acid," Chem. Comm. 6: 705-706 (1996).

Kimura, et al., "Sugar-induced conformational changes in boronic acid-appended poly(L- and D-lysine)s and sugar-controlled orientation of a cyanine dye on the polymers," J. Chem. Soc. Perkin Trans. 2 10: 1884-1894 (1995).

Liu, et al., "New ligands for boronate affinity chromatography," J. Chromatography A 687: 61-69 (1994).

Malan, et al., "Synthesis of 4-borono-L-phenylalanine," Synlett 2: 167-168 (1996).

Miyazaki, et al., "Boronate-containing polymer as novel mitogen for lymphocytes," Biochem. Biophys. Res. Comm. 195: 829-836 (1993).

Ohadi, et al., "Posterior capsule opacification," Curr. Opin. Ophthalmol. 2: 46-52 (1991).

Pale-Grosdemange, et al., "Formation of self-assembled monolayers by chemisorption of derivatives of oligo (ethylene glycol) of structure $HS(CH2)_{11}(OCH_2CH_2)_mOH$ on gold," J. Am. Chem. Soc. 113: 12-20 (1991).

Rice, et al., "A comparative evaluation of Poloxamer 407 and oxidized regenerated cellulose (Interceed [TC7]) to reduce postoperative adhesion formation in the rat uterine horn model," Fertility and Sterility 59: 901-906 (1993).

Shiino, et al., "Amine effect on phenylboronic acid complex with glucose under physiological pH in aqueous solution," J. Biomater. Sci. 7: 697-705 (1996).

Shiino, et al., "A self-regulated insulin delivery system using boronic acid gel," J. Intelligent Mater. Syst. Struct. 5: 311-314 (1994).

Shiino, et al., "Preparation and characterization of a glucose—responsive insulin-releasing polymer device," Biomaterials 15(2): 121-128 (1994).

Singhal, et al., "Boronate affinity chromatography," in Advances in Chromatography (Giddings, et al., ed.) 31:293-335 (1992).

Singhal, et al., "New ligands for boronate affinity chromatography: synthesis and properties," J. Chromatography 543: 17-38 (1991).

Steinleitner, et al,. "An evaluation of flowgel as an intraperitoneal barrier for prevention of postsurgical adhesion reformation," Fertility and Sterility 57: 305-308 (1992).

West, et al., "Comparison of covalently and physically cross-linked polyethylene glycol-based hydrogels for the prevention of postoperative adhesions in a rat model," Biomaterials 16: 1153-1156 (1995).

Wulff, "Selective binding to polymers via covalent bonds. The construction of chiral cavities as specific receptor sites" Pure and Applied Chemistry 54: 2093-2102 (1982).

US 7,029,688 B2

METHODS AND COMPOSITIONS TO PREVENT FORMATION OF ADHESIONS IN BIOLOGICAL TISSUES

CROSS REFERENCE TO RELATED APPLICATION

This application is a divisional of U.S. Ser. No. 09/140,781 filed on Aug. 27, 1998, now U.S. Pat. No. 6,596,267 by Jeffrey A. Hubbell, Natalie D. Winblade, and Donald L. Elbert and entitled "Methods and Compositions to Prevent Formation of Adhesions in Biological Tissues", which claims priority to provisional patent application Ser. No. 60/056,854 filed on Aug. 27, 1997 by Jeffrey A. Hubbell, Natalie D. Winblade, and Donald L. Elbert and entitled "Steric Protection of Biological Surfaces by the Adsorption of Copolymers Containing Poly(ethylene glycol) and Phenylboronic Acid".

STATEMENT REGARDING FEDERALLY FUNDED RESEARCH

The U.S. Government has certain right in this invention by virtue of a National Science Foundation Graduate Fellowship to Natalie Winblade and NIH Grant number HL56297 to Jeffrey Hubbell.

FIELD OF THE INVENTION

The present invention relates to methods and polymeric compositions for preventing the formation of tissue adhesions following surgical procedures or injury.

BACKGROUND OF THE INVENTION

Many pathological conditions result from the adhesion of proteins or cells to extracellular matrix, membranes, or other surfaces in the body. For example, damage to tissue surfaces after peritoneal surgery can result in formation of fibrinous attachments between tissues. G. dizerega, *Fertility and Sterility* 61:219–235 (1994); G. Holtz, *Fertility and Sterility* 41:497–507 (1984). These adhesions can have severe consequences including pain, bowel obstruction, and infertility. Adhesion can also occur as a result of cataract surgery. Residual lens epithelial cells migrate onto the posterior lens capsule, resulting in formation of a secondary cataract, referred to as posterior capsule opacification, and subsequent reduction in vision. D. Apple et al., *Survey of Ophthalmology* 37:73–116 (1992).

These conditions result from disruption of the naturally occurring surface of a biological tissue through surgical manipulation or external injury, followed by direct contact of one such disrupted biological surface with another biological surface, and then formation of a cellular adhesion that connects the adjacent tissues. Adhesions are scar tissue bridges that often connect to opposing organs, for example, restricting organ movement and function as well as causing pain.

One approach to prevention of adhesions has involved using a physical barrier that isolates the biological surfaces from each other. Attempts to prevent surface to surface contact of tissues have met with varying levels of success. In some cases, the materials did not remain in intimate contact with the treated biological surface for a sufficient period of time. In other cases, application of the barrier materials required extensive surgical manipulation in order to cover inaccessible tissue surfaces.

Most previous work in preventing adhesions has been in the field of gynecological surgery. Solid, liquid, and gel materials have been used. Solid treatments presumably work by providing a barrier between the damaged surface and other cells. The most popular of these materials are oxidized regenerated cellulose and expanded polytetrafluoroethylene, but use of these barriers has resulted in questionable efficacy, due to the requirement for extensive surgical manipulation, sometimes including additional surgery, nonadherence of the barrier to the surface, and immune response.

Liquid materials have included high molecular weight dextran solutions, hyaluronic acid, in liquid or gel form, and Ringer's lactate. These materials may work by preventing tissue damage in the first place and/or by "floating" the tissues, but the materials can make surgical manipulation difficult and all of the materials have shown questionable efficacy.

Gel materials have included fibrin glues, a triblock copolymer of polyethylene glycol (PEG) and polypropylene glycol (PPG) which gels at physiological temperatures, and a PEG-co-lactic acid (PEG-PLA) hydrogel. U.S. Pat. Nos. 5,410,016, 5,626,863, and 5,567,435, to Hubbell et al., disclose PEG-PLA hydrogels useful for adhesion prevention. These treatments presumably work by forming a barrier over the injured surface. The fibrin glue has not been tested on lysed adhesions and it may induce inflammatory response. P. De Iaco et al., *Fertility and Sterility* 62:400–404 (1994); L. Adamyan et al., *International Journal of Fertility* 36:76–88 (1991). The triblock copolymer may be cleared from the wound site too quickly because it does not adhere specifically to surfaces. V. Montgomery Rice et al., *Fertility and Sterility* 59:901–906 (1993); A. Steinleitner et al., *Fertility and Sterility* 57:305–308 (1992). Application of the PEG-PLA hydrogel requires access to and specific treatment of each surface involved, as well as UV irradiation for the gel to form. J. West et al., *Biomaterials* 16:1153–1156 (1995).

Research on the prevention of posterior capsule opacification by blocking adhesion of epithelial cells to the posterior capsule has focused on causing firm contact between an implanted intraocular lens and the posterior capsule, presumably mechanically blocking the migration of cells into the visual axis of the posterior capsule. D. Apple et al., *Survey of Ophthalmology* 37:73–116 (1992); C. Ohadi et al., *Current Opinion in Ophthalmology* 2:46–52 (1991). The mechanism of this technique has yet to be confirmed, and clinical results vary.

Elbert has investigated self assembling treatments which sterically protect the underlying surfaces to allegedly prevent adhesions. D. L. Elbert et al., *Chemistry and Biology* 5:177–183 (1998). Elbert used copolymers containing PEG and lysine, having a comb geometry of a poly(lysine) backbone with PEG sidechains or a dendrimer geometry of PEG attached to a lysine dendrimer. The cationic copolymers may adsorb to many biological surfaces, presumably due to electrostatic interactions, while the PEG molecules presumably sterically hinder the approach of proteins and cells to the surfaces. Other research in the area has included using PEG to sterically protect surfaces by covalently adding PEG to the surface (S. Dunn et al., *Pharmaceutical Research* 11:1016–1022 (1994)), entrapping PEG in the surface (N. Desai et al., *Biomaterials* 13:505–510 (1992)), applying PEG to the surface within a gel (A. Steinleitner et al., *Fertility and Sterility* 57:305–308 (1992); J. West et al., *Biomaterials* 16:1153–1156 (1995)), and adsorbing PEG copolymers to surfaces by adding cationic moieties to the PEG (D. L. Elbert et al., *Chemistry and Biology* 5:177–183 (1998)).

A biocompatible material that would prevent surface to surface contact by spontaneously adhering directly to a biological surface, in sufficient quantities to protect the surface, would provide a great advantage over all of the aforementioned treatments. The material would also present a cell and protein resistant outer layer that would minimize interactions with other surfaces during healing.

It is therefore an object of the present invention to provide polymeric materials that can be applied to tissues, in a very short time period, to protect the tissues from tissue to tissue interactions, such as adhesion.

It is a further object of the present invention to provide polymeric materials which are biocompatible and resistant to degradation for a specific time period.

It is a further object of the present invention to provide methods for making and using compositions for inhibiting tissue to tissue contact and adhesion within the body.

SUMMARY OF THE INVENTION

Methods and compositions are provided that form a self assembling layer on biological surfaces. The materials prevent adhesion via steric hindrance and inhibit direct contact between adjacent tissues. The materials are easy to apply to the tissue surface and exhibit lasting intimate contact with the tissue surface. These materials are copolymers of a polymer including boronate groups such as phenylboronic acid, which adsorb onto biological surfaces, and a polymer which is nonadsorbing, and adhesion resistant, such as polyethylene glycol, which interferes sterically with surface contact between tissues. The copolymers spontaneously adsorb to many biological surfaces containing acid or hydroxyl groups and remain for a finite period of time, preferably a matter of days, to sterically protect the surface while it heals.

The compositions can be applied to isolated tissue or to tissue during surgery or by means of a catheter or other less invasive device, for example during angioplasty or atherosclerosis surgery. The compositions are useful for blocking adhesion and immune recognition and thereby aid in the prevention of postoperative adhesions, protection of injured blood vessels from thrombosis and intimal thickening relating to restenosis, and decrease the extent of metastasis of tumor cells. The materials can be used as barriers to prevent the interaction of one cell or tissue with another cell or tissue, and as carriers for bioactive species. A wide variety of biological and nonbiological surfaces, with different geometries, can also be coated with these polymeric materials.

DETAILED DESCRIPTION OF THE INVENTION

Compositions for coating surfaces to minimize or prevent tissue to tissue contact and tissue adhesion, and methods of preparation and use thereof, are disclosed. The compositions can be used, for example, to coat tissue or other surfaces to alter cell or tissue interaction with a surface contacting the cell or tissue. The compositions can also be used to deliver therapeutic, prophylactic, or diagnostic substances or to encapsulate cells. Another use for the compositions is to minimize or prevent undesirable cell proliferation, decrease the risk of thrombosis, and decrease inflammation.

As defined herein, "tissue" includes tissues removed from the body and tissues present in the body, and also includes cells and cell aggregates. This term also refers to treated tissue, such as tissue heart valves, blood vessels and membranes, where the tissue is no longer living and has been chemically fixed, or a cryopreserved blood vessel or other tissue.

I. Compositions

The following definitions apply to the copolymers described herein. Block copolymers are defined as copolymers in which a polymeric block is linked to one or more other polymeric blocks. This is distinguished from random copolymers, in which two or more monomeric units are linked in random order to form a copolymer. Brush copolymers (as in a bottle brush) are copolymers which have a backbone of one composition and bristles of another. These copolymers are also known as comb copolymers. The terms brush and comb are used interchangeably. Dendritic polymers, also known as dendrimers or starburst polymers, are polymers which include a core molecule which is sequentially reacted with monomers with three or more reactive groups, such that at each sequential coupling step, the number of reactive groups at the ends of the polymer increases, usually exponentially. A dendron is a subunit of a dendrimer, the structure resulting from sequential reactions starting with a core containing only reactive group. As used herein, molecular weight refers to weight average molecular weight, unless otherwise specified. As used herein, PEG is an abbreviation for polyethylene glycol, also known as polyethylene oxide or polyoxyethylene. The phrase "(meth) acrylic" refers to either acrylic or methacrylic groups.

A. Bifunctional Copolymers

These materials are copolymers which contain two functionalities. One functionality adheres the copolymer to one surface and another functionality presents an adhesion resistant outer layer to other tissue surfaces. The duration of protection provided by the copolymer is dependent on the rates of desorption and degradation of the copolymer.

The copolymers can have any of a number of geometries, including block copolymers where both segments are linear, dendritic copolymers where the adsorbing segment is dendritic, and comb copolymers where the adsorbing segment is the copolymer backbone. The size, number of, and relative length of each segment can be varied, as required.

1. The Adherent Functionality

The adherent functionality of the copolymers is provided by a boronate group that can adhere to a surface, such as through interaction with diols of surface polysaccharides. Useful boronates include phenylboronic acid (PBA), 2-carboxyethaneboronic acid, 1,2-dicarboxyethaneboronic acid, β,β'-dicarboxyethaneboronate, β,γ-dicarboxypropaneboronate, 2-nitro- and 4-nitro-3-succinamidobenzene boronic acids, 3-nitro-4-(6-aminohexylamido)phenyl boronic acid, {4-[(hexamethylenetetramine)methyl]phenyl}boronic acid, 4-(N-methyl)carboxamidobenzene boronic acid, 2-{[(4-boronphenyl)methyl]-ethylammonio}ethyl and 2-{[(4-boronphenyl)methyl]diethylammonio}-ethyl groups, succinyl-3-aminophenylboronic acid, 6-aminocaproyl-3-aminophenylboronic acid, 3-(N-succinimidoxycarbonyl) aminophenylboronate, p-(ω-aminoethyl)phenylboronate, p-vinylbenzeneboronate, N-(3-dihydroxyborylphenyl)succinamic acid, N-(4-nitro-3-dihydroxyborylphenyl)succinamic acid, O-dimethylaminomethylbenzeneboronic acid, 4-carboxybenzeneboronic acid, 4-(N-octyl)carboxamidobenzeneboronic acid, 3-nitro-4-carboxybenzeneboronic acid, 2-nitro-4-carboxybenzeneboronic acid, 4-bromophenylboronate, p-vinylbenzene boronate, 4-(ω-aminoethyl)phenylboronate, catechol [2-(diethylamino)carbonyl, 4-bromomethyl]phenyl boronate, and 5-vinyl-2-dimethylaminomethylbenzeneboronic acid. These boronate containing groups differ in terms of pKa, spacer arms, or different coupling options associated with them.

In a preferred embodiment, the boronate group is provided by phenylboronic acid (PBA) which is known to form reversible conjugates with coplanar diols, such as closed ring carbohydrates and polyvinyl alcohol, as well as with acidic ligands such as dicarboxylic acids and α-hydroxy carboxylic acids. PBA has a strong affinity to many biological surfaces, since the surfaces of cells and extracellular matrix are rich in proteoglycans and other carbohydrate moieties, as well as many acidic moieties. PBA also has been shown to form reversible complexes with glycoconjugates on endothelial cell membranes (T. Aoki et al., *Journal of Biomaterials Science Polymer Edition* 7:539–550 (1995)) and lymphocyte membranes (H. Miyazaki et al., *Biochemical and Biophysical Research Communications* 195:829–836 (1993)). The "working pH" of the PBA moieties in each copolymer can be adjusted by placing amine groups in proximity to the PBA groups or by placing electron withdrawing groups within the PBA moiety itself. A PBA moiety with a nitro group in the ring and a succinamic acid functionality has been synthesized by Singhal et al., *Journal of Chromatography* 543:17–38 (1991), and could be coupled to amine groups using carbonyldiimidazole or N-hydroxysuccinimide. A PBA moiety that has an internal coordinate bond, making the boron tetrahedral, and that has a bromomethyl group that could be reacted with the thiol of cysteine was synthesized by X.-C. Liu et al., *Journal of Chromatography A* 687:61–69 (1994). A polymer precursor with a very low pKa, 5-vinyl-2-dimethylaminomethylbenzeneboronic acid that could be used in creating random copolymers containing PBA was synthesized by G. Wulff, *Pure and Applied Chemistry* 54:2093–2102 (1982).

2. The Adhesion Resisting Functionality

The nonadsorbing, adhesion resistant segment of the copolymer described herein consists of any of many water soluble polymers that are poorly cell adhesive. Neutral, highly hydrophilic polymers tend to be the best at resisting protein and cell adhesion. Suitable non tissue binding polymers include polyalkylene oxides, mixed polyalkylene oxides having a solubility of at least one gram/liter in aqueous solutions, water soluble polysaccharides, such as dextrans and agaroses, polyvinyl alcohol, poly-N-vinyl pyrrolidone, noncationic poly(meth)acrylates, such as poly(hydroxyethyl methacrylate), and combinations thereof. Anionic hydrophilic polymers such as polyacrylic acid can also be used, provided that the segment does not contain positive groups such as lysines, or else the polymer may precipitate with itself.

The adhesion resisting functionality is most preferably polyethylene glycol (PEG). PEG is very hydrophilic, associating with as many as 5.5 water molecules per ethylene oxide unit at 23° C. P. Claesson et al., *Journal of Colloid and Interface Science* 117:366–374 (1986). PEG is also very flexible (W. B. Russel et al., Colloidal Dispersions (Cambridge University Press, New York, 1989)), and a small surface density of PEG can shield a large area. C. Pale-Grosdemange et al., *Journal of the American Chemical Society* 113:12–20 (1991). PEG elongates and rotates freely in water, excluding large amounts of space and resisting adsorption. There is much evidence that surfaces containing PEG are sterically protected. For example, surfaces containing PEG have been shown to greatly stabilize colloids, to resist protein adhesion much better than glucose or hydroxyl covered surfaces in vitro, to resist fibroblast adhesion in vitro, to induce less inflammation and fibrotic response than implants without PEG in vivo, and to reduce uptake of microspheres by liver cells in vivo.

B. Additional Polymeric Components

Additional polymeric components, domains, linking groups, and bioactive, prophylactic, or diagnostic materials can be added to this basic two domain structure. Examples of additional polymeric components for attachment of linking groups, and bioactive, prophylactic, or diagnostic materials include PEG, polyacrylic acid, poly-N-vinyl pyrrolidone, hyaluronic acid, and other polysaccharides. Other domains that can be incorporated include bioadhesive molecules, domains which convert from a binding domain to a nonbinding domain in vivo, and domains which convert from a nonbinding domain to a binding domain in vivo, as described in U.S. Pat. No. 5,410,016 to Hubbell et al. Examples of linking groups include biodegradable linkages, such as anhydride, ester, amide, and carbonate linkages. Examples of bioactive materials include proteins, sugars and polysaccharides, organic compounds with drug activity, and nucleic acids. The domains and/or linkages can selectively adhere to particular types of cells or molecules or be selectively degraded by enzymatic or nonenzymatic means. The domains may be a third type of polymer, for example, a biodegradable polymer such as a polyanhydride, polyhydroxy acid or polycarbonate. A peptide such as RGD, or even a single amino acid, which is used to target a polyamino acid for cleavage by an enzyme, can be incorporated into the polymer structure, to direct attachment, as discussed in more detail below.

Photopolymerizable substituents, including acrylates, diacrylates, oligoacrylates, dimethacrylates, or oligomethacrylates, and other biologically acceptable photopolymerizable groups, can also be added to the polymeric materials. These can be used to further polymerize the polymer once it is in contact with tissue or other surfaces, which can result in improved adherence to the surface.

C. Bioactive, Prophylactic, or Diagnostic Species

Bioactive, prophylactic, or diagnostic species can be attached to the copolymers, either covalently or ionically, or by mixing the species with the polymeric material, preferably before it is applied to the tissue.

A wide variety of biologically active materials can be encapsulated or incorporated, including proteins such as antibodies, receptor ligands and enzymes, peptides such as adhesion peptides, sugars, oligosaccharides, and polysaccharides, organic or inorganic drugs, nucleotides and nucleic acids, and cells, tissues or subcellular organelles or other subcellular components.

Bioactive species may be used to target adhesion of the polymeric material, to effect a biological activity at the polymeric material and tissue interface, or to effect an activity when the bioactive species is released during degradation of the polymeric material.

Exemplary ligands include the pentapeptide Tyr-Ile-Gly-Ser-Arg (YIGSR), which supports endothelial, smooth muscle cell, and fibroblast adhesion, but not platelet adhesion; and the tetrapeptide Arg-Glu-Asp-Val (REDV), which has been shown to support endothelial cell adhesion but not that of smooth muscle cells, fibroblasts, Or platelets, as described in Hubbell et al., *BioTechnology* 9:568–572 (1991). YIGSR, from laminin, binds to receptors on endothelial cells, but not on blood platelets. Thus, application of a copolymer having conjugated thereto the peptide YIGSR to a damaged vessel wall would be expected to block thrombosis on the vessel wall but not to block reendothelialization from the surrounding undamaged vessel wall.

Exemplary diagnostic agents include diagnostic enzymes and radiolabelled and fluorescent compounds.

II. Methods of Making Copolymers

A. AB Block Copolymers

An AB block copolymer, where A refers to the adsorbing segment and B refers to the non-adherent section, can be made starting from a peptide prepared using standard techniques, such as Fmoc peptide synthesis. For example, a cysteine residue can be inserted in the peptide for selective reaction with monomethoxy-PEG-vinylsulfone (monomethoxy-PEG-$SO_2CHCH_2$). Lysine residues can be inserted in the peptide for reductive amination with 4-formylphenylboronic acid. Alternatively, 4-carboxyphenylboronic acid can be synthesized as described by T. Kimura et al., *Journal of the Chemical Society Perkin Transactions* 2 10:1884–1894 (1995) and references therein. This can be converted to the acid chloride with $SOCl_2$ or activated with a group such as carbonyldiimidazole or N-hydroxysuccinimide, then reacted with lysine residues. These two techniques allow lysines that are not derivatized to be intermixed with lysines that are bound to PBA groups. This can be achieved by using a low acid cleavable group, such as a 4-methyltrityl group, to protect lysines that will be reacted with PBA and using a conventional protecting group, such as t-butoxycarbonyl, to keep remaining lysines protected until the peptide-PBA compound is cleaved in 95% trifluoroacetic acid. Another alternative is to place aspartate or glutamate residues in the peptide, activate the carboxyl groups with carbonyldiimidazole or N-hydroxysuccinimide, and then react the activated carboxyl groups with 3-aminophenylboronic acid. Another option is to place serine or threonine in the peptide, react the hydroxyl groups with bisoxirane, and react the product with 3-aminophenylboronic acid. In all cases, reactions with the N- and C-terminus can be eliminated by placing N-acetyl glycine at the N-terminus of the peptide and using a peptide synthesis resin that yields an amide C-terminus. Also, a glycine spacer can be placed between the cysteine residue and the other residues, to make the cysteine more accessible to reaction with PEG. Other well defined polymer geometries such as ABA or oligo(AB) can also be synthesized using these methods.

B. A(dendrimer)B Block Copolymers

An A(dendrimer)B block copolymer of PEG and PBA can be synthesized from a monomethoxy-PEG-lysine(dendrimer) compound as described by D. L. Elbert et al., *Chemistry and Biology* 5:177–183 (1998). After the final generation of lysines has been coupled to the compound, the lysines can be derivatized with PBA using any of the methods described above, including a method whereby a desired amino acid is reacted with the ϵ-amino group of lysine and then reacted with the PBA moiety of the newly added amino acid.

C. A-g-B Comb Copolymers

An A-g-B comb copolymer can be synthesized starting from poly(lysine) or starting from a random copolymer containing PBA. Starting from poly(lysine), PBA groups can be added by any of the methods described in the AB block copolymer section (the ratio of PBA reactants to lysine amines present can be varied for the desired ratio of PBA to lysines). Monomethoxy-PEG can then be added by activating the PEG with carbonyldiimidazole or N-hydroxysuccinimide, and reacting the product with remaining free lysines in the copolymer. Alternatively, a random copolymer can be synthesized that contains PBA and amine groups, such as those synthesized by D. Shino et al. (D. Shino et al., *Journal of Biomaterials Science Polymer Edition* 7:697–705 (1996) and references therein), but incorporate a group containing a primary amine, such as 4-vinylaniline. Monomethoxy-PEG can then be grafted as just described.

D. Optimization of the Polymeric Material for Specific Applications

The biological performance of the copolymers can be optimized by altering the structure of the copolymers, the ratio of the number of tissue binding polymers to nonbinding polymers, and the ratio of the mass of the tissue binding polymers to nonbinding polymers.

In some cases, polymeric materials that degrade by multiple mechanisms can be used. For example, degradation by nonenzymatic hydrolysis will depend primarily upon the accessibility of the polymeric material to water and the local pH. Given that pH and water concentration are similar throughout many parts of the body, this would result in a decrease in repellency as a function of time. As another example, if the degradable region is cleaved by an enzyme which is not highly regulated but is present in body fluids at a more or less constant level, the rate of loss of repellency depends primarily upon time. As another example, if the degradable region is cleaved by an enzyme which is more highly regulated, the rate of loss of repellency will be a function of enzyme activity. For example, during migration, many types of cells express the proteases plasmin or collagenase. Incorporation of a region cleaved by a protease into the polymer allows the polymer to be degraded by cells migrating onto a surface covered with the polymer, so that they can attach to and recolonize the surface.

The biological performance of these polymeric materials depends upon their structure. Specific features affecting biological performance include degree of binding to the tissue, degree of repulsion of opposing tissues, duration of binding to the tissue, duration of repulsion of opposing tissues, and the mode of loss of binding or repulsion. Specific features of polymeric material structure include the chemical composition of tissue binding and nonbinding domain, the ratio of the mass of binding to nonbinding domains, the number of binding to nonbinding domains, the inclusion of sites that are particularly susceptible to nonenzymatic hydrolysis, the inclusion of sites that are particularly susceptible to enzymatic hydrolysis, and the inclusion of sites with particular biological affinity or activity.

The degree of protection of the treated surface depends on the length of time that the copolymer remains on the surface. For example, the rate of copolymer desorption from the surface depends on the number of adhesive (PBA) groups and on the size and number of non-adhesive (PEG) groups in the copolymer. Polymers with lower relative amounts of PBA would be expected to cause less activation of cells, since polymers with higher relative amounts of PBA will tend to crosslink more receptors, thereby creating a signal for cell activation.

Degradable links can be introduced within the copolymer by introducing ester moieties, such as lactic acid, added by ring opening polymerization of D,L-lactide, or enzyme cleavage sequences, in the backbone or in the backbone linkage to PEG to affect the in situ lifetime of the copolymer. D-amino acids can be used in place of any L-amino acids to reduce the rate of enzymatic hydrolysis in vivo and perhaps to reduce immune response. The boronic acid groups of PBA can be protected as described by Malan et al. or James et al. C. Malan et al., *Synlett* 2:167–168 (1996); T. D. James et al. *Chemical Communications* 6:705–706 (1996).

All of these parameters can be varied in the design of the copolymers described herein, and used in various combinations as necessary for the specific medical purpose for which the copolymer is needed.

III. Methods of Using the Copolymers

A. Prevention of Adhesions and Abnormal Proliferation

The copolymers can be used to treat any site at which undesirable adhesions could form. These include primary, and especially secondary, adhesions in the abdominal cavity, including intestine to intestine, and intestine to peritoneum; in the pelvic cavity, including adhesion of the uterus, ovaries or fallopian tubes to other structures including each other and the pelvic wall; in tendons and their support structures, including tendon to pulley or to synovium; in the repair of nerve sheaths; in repair of the spinal column or disks; in the pericardium; in treatment of joints for inflammation and to prevent pannus formation; and in any other situation in which adhesions form which impair function or cause pain. The compositions can also be used to prevent undesirable tissue proliferation, as in restenosis, repair of keloid or hypertrophic scars, hypertrophy which obstructs ducts, such as benign prostatic hypertrophy, and endometriosis.

Alone or in combination with prevention of adhesions and cellular proliferation, the copolymers should be useful for delivery of bioactive compounds; prevention of thrombus formation at blood vessel surfaces, for example, following angioplasty; alteration of cellular attachment, especially to prevent cellular attachment, and therefore decrease metastasis of tumor cells; and coating of prosthetic implants such as heart valves and vascular grafts derived from processed tissues.

The polymeric materials can be locally or topically applied for local or systemic drug delivery. Typically, materials will be applied by spraying or injecting a very thin layer (usually on the order of monolayers of polymeric material) onto the surface to be coated. Methods for applying the polymeric materials in this manner are known to those skilled in the art.

The copolymers can be applied as a solution at the time of or shortly after tissue injury to protect the damaged surfaces during healing. This could be useful following virtually any surgery that is known to be followed by problematic wound healing responses, especially where cells, tissues, or scar tissue are typically laid down in the damaged areas, for example, cataract surgery, surgery in the peritoneal cavity, balloon angioplasty, cancer surgery, and organ transplantation. The copolymers are also useful for application to tissues which have been cauterized, stapled, dilated, treated by heating or cooling, treated by ionizing radiation, or treated by optical irradiation.

The copolymers can be applied using a catheter or using other minimally invasive techniques.

B. Coating of Non Biological Surfaces

The polymeric materials can also be applied to a nonbiological surface, such as one containing hydroxyl or carboxylic acid groups, intended to be placed in contact with a biological environment. Such surfaces include, for example, catheters, prosthetics, vascular grafts, contact lenses, intraocular lenses, other implants and ultrafiltration and dialysis membranes, and containers for biological materials. All of these surfaces include an entity such as, for example, a cellulose derivative that will interact with the adherent functionality. Additionally, cell culture dishes, or portions thereof, can be treated to minimize adhesion of cells to the dish. Cell culture dishes treated in this manner only allow spreading of anchorage dependent cells (cells which must be anchored to a solid support in order to spread) in those areas which are not treated.

Deposition of biological matter on metal surfaces can be minimized by coating the surfaces with the polymeric materials. The compositions could effectively bond to surfaces containing metal oxides such as iron oxide, titanium oxide and silicon oxide. The metals are treated with the copolymer as a part of conduit or device manufacture, or are treated in situ, following assembly of the conduit or device, or as part of the normal operation of the device. The copolymers may be applied by adsorption of the polymeric materials from a liquid solution, or by spraying. Removal of the polymer from the metal via a change in pH, or other means, may also be used as a cleaning step as a part of the normal operation of a device using this technology. The copolymer layer can then be reapplied to the metal, resulting in a resumption of the protein-repelling properties at the treated metal surface.

The methods and materials are further described by the following, nonlimiting examples.

Methods and Materials

N,N-dimethylformamide, dichloromethane (DCM), piperidine, diisopropylethylamine, and trifluoroacetic acid were obtained from Perseptive. Amino acid residues, HOBT, HBTU, and Novasyn TGR resin were from Novabiochem. Peptides were synthesized on a Millipore 9050 Plus Peptide Synthesizer using standard Fmoc chemistry. Tris(2-carboxyethyl)phosphine-HCl (TCEP) was from Pierce. Monomethoxy-PEG-vinylsulfone, starting material molecular weight 5000, was from Shearwater. Sodium bicarbonate, sodium phosphate monobasic and dibasic, and potassium phosphate monobasic were from Mallinckrodt. Sodium chloride was from Fisher. EDTA was from Sigma. Ether and potassium chloride were from EM Science. Thiopropyl Sepharose™ 6B gel (which presents free thiols upon reduction of disulfide bonds) was from Pharmacia. All other chemicals were from Aldrich. The water that was used was deionized. Dialysis membrane was 3500 molecular weight cut off (MWCO) SpectralPor from Spectrum. Dialysis and filter membranes were from VWR. $^1$H NMR was performed on a 400 MHz JEOL JNM-GX400 FTNMR Spectrometer from Oxford Instruments. All NMR samples were dissolved in $D_2O$ at about 10 mg/mL.

Thiol content was monitored by a modified Ellman's assay. 5,5'-dithiobis(2-nitrobenzoic acid) was dissolved to 10 mM in a 0.1 M phosphate, 0.5 M NaCl, 5 mM EDTA buffer at pH 7.27 (modified Ellman's reagent). 30 μL of a sample was added to 770 μL of the buffer and 200 μL of Ellman's reagent. 30 μL of the result was added to 770 μL of buffer and allowed to react for 5 min. Then the absorbance at 412 nm was measured and subtracted from a blank which used 30 μL of the same buffer as the sample.

EXAMPLE 1

The Reductive Amination of Lysine with Phenylboronic Acid

N-acetyl-Gly)-Cys(Trt)-Gly-(Lys(Mtt))$_5$ was synthesized on 2.7 g of PEG-polystyrene resin with 0.2 mmol/g functionality (the resin used yields an amide C-terminus). The lysine protecting groups were deprotected by soaking the resin in 1% trifluoroacetic acid, 5% triisopropylsilane in DCM for about 3 minutes then filtering. This was repeated ten times and the material was then washed with DCM. The lysine was then desalted by adding 10 times excess triethylamine in DCM and then rinsing with DCM. The peptide-resin, 1.05 equivalents of 4-formylphenylboronic acid and 10 equivalents of sodium triacetoxyborohydride (based on the number of lysines present) were placed under argon and dissolved with anhydrous DCM so the peptide was 2 mM (not all of the reactants dissolved completely). The reaction was kept under argon and stirred for 17.5 h. Then the solution was rinsed with DCM, rinsed copiously with water saturated with sodium bicarbonate, rinsed with water while filtering (0.45 μm Gelman FP Vericel filter), and then vacuum dried. The peptide-PBA compound was then cleaved from the resin by adding about 22 mL of 85% trifluoroacetic acid, 5% phenol, 5% $H_2O$, and 5% triethylsilane. The resin was cleaved for 1.5 hours with swirling, then the solution was filtered into ice-cold ether. The precipitate was collected, rinsed with ether, and vacuum dried.

EXAMPLE 2

Grafting of PEG to the Peptide-PBA Compound 2.67 g of thiopropyl Sepharose™ 6B gel was swollen in water and then rinsed copiously with water. A 0.1 M phosphate, 0.5 M NaCl, 5 mM EDTA, 1 mM TCEP, pH 7.00 buffer was sonicated. 10.7 mL of buffer and 0.46 g of TCEP were added to the gel, placed under argon, and swirled for 1 hour. The result was rinsed copiously with the previously mentioned buffer, poured into a chromatography column, and greater than 3 bed volumes of buffer was flowed through by gravity. The column was then capped. The peptide-PBA compound of Example 1 was added to 0.09 g of TCEP, and 6 mL of buffer. The solution was stirred and 300 μL was reserved (as "free mL of buffer 3 times. All eluents were combined and dialyzed against phosphate buffered saline 2 times, saline 7 times, and water 4 times, for a total of 5 days. The dialyzed solution was filtered through a 0.2 μm Acrodisc™ PF syringe filter and lyophilized.

The results of NMR and Ellman's assays demonstrate the synthesis of the molecule shown schematically as:

where an average of 1.7 PBA moieties are present per peptide.

The teachings of the references cited herein are specifically incorporated herein. Modifications and variations of the present invention will be obvious to those skilled in the art from the foregoing detailed description and are intended to be encompassed by the following claims.

What is claimed is:

1. A method for altering cell or tissue interaction with a surface comprising applying to the surface an effective amount of a copolymer comprising an adsorbing segment containing boronate groups and an adhesion resistant segment,
   wherein the copolymer is selected from the group consisting of block copolymers where both segments are linear, dendritic copolymers where the adsorbing segment is dendritic and brush copolymers where the adsorbing segment is the copolymer backbone,
   wherein the adhesion resistant segment is effective to prevent cellular attachment or deposition of biological material on a surface coated with the copolymer.

2. The method of claim 1, wherein the copolymer is applied in an amount effective to minimize or prevent tissue adhesion.

3. The method of claim 1, wherein the copolymer is applied in an amount effective to decrease the risk of thrombosis, decrease inflammation, or decrease the abnormal proliferation of cells.

4. The method of claim 1, wherein the copolymer is applied in an amount effective to enhance wound healing.

5. The method of claim 1, wherein the copolymer is applied in an amount effective for the delivery of a bioactive, prophylactic, or diagnostic agent.

6. The method of claim 1, wherein the surface is the surface of a prosthesis or other implantable device.

7. The method of claim 1, wherein the surface is a surface of a cell or tissue.

8. The method of claim 1, wherein the surface is a region where tissue has been injured.

9. The method of claim 1, wherein the copolymer is applied at the time of or shortly after tissue injury.

10. The method of claim 1, wherein the copolymer is applied using a catheter or other minimally invasive technique.

11. The method of claim 1, wherein the adsorbing segment comprises a boronate group selected from the group consisting of phenylboronic acid (PBA), 2-carboxyethaneboronic acid, 1,2-dicarboxyethaneboronic acid, β,β'-dicarboxyethaneboronate, β,γ-dicarboxypropaneboronate, 2-nitro- and 4-nitro-3-succinamidobenzene boronic acids, 3-nitro-4-(6-aminohexylamido)phenyl boronic acid, {4-[(hexamethylenetetramine)methyl]phenyl}boronic acid, 4-(N-methyl)carboxamidobenzene boronic acid, 2-{[(4-boronphenyl)methyl]-ethylammonio}ethyl and 2-{[(4-boronphenyl)methyl]diethylammonio}-ethyl groups, succinyl-3-aminophenylboronic add, 6-aminocaproyl-3-aminophenylboronic acid, 3-(N-succinimidoxycarbonyl)aminophenylboronate, p-(ω-aminoethyl)phenylboronate, p-vinylbenzeneboronate, N-(3-dihydroxyborylphenyl)succinamic acid, N-(4-nitro-3-dihydroxyborylphenyl)succinamic acid, O-dimethylaminomethylbenzeneboronic acid, 4-carboxybenzeneboronic acid, 4-(N-octyl)carboxamidobenzeneboronic acid, 3-nitro-4-carboxybenzeneboronic acid, 2-nitro-4-carboxybenzeneboronic acid, 4-bromophenylboronate, p-vinylbenzene boronate, 4-(ω-aminoethyl)phenylboronate, catechol [2-(diethylamino)carbonyl, 4-bromomethyl]phenyl boronate, and 5-vinyl-2-dimethylaminomethylbenzeneboronic acid.

12. The method of claim 1, wherein the adsorbing segment comprises phenylboronic acid.

13. The method of claim 1, wherein the adhesion resistant segment is selected from the group consisting of polyalkylene oxides, mixed polyalkylene oxides having a solubility of at least one gram/liter in aqueous solutions, water soluble polysaccharides, polyvinyl alcohol, poly-N-vinyl pyrrolidone, noncationic polyacrylates, noncationic polymethacrylates, and mixtures and copolymers thereof.

14. The method of claim 1, wherein the adhesion resistant segment is polyethylene glycol.

15. The method of claim 1, wherein the copolymer is a block copolymer.

16. The method of claim 1, wherein the copolymer is a brush copolymer.

17. The method of claim 1, wherein the copolymer is a dendritic copolymer.

18. The method of claim 1, further comprising a pharmaceutically acceptable carrier.

19. The method of claim 1, further comprising a biodegradable linkage.

20. The method of claim 1, wherein the copolymer further comprises a bioactive, therapeutic, or diagnostic agent.

21. The method of claim 20, wherein the agent is chemically coupled to the copolymer.

22. The method of claim 1, wherein the adsorbing segment comprises electron withdrawing groups so that the effective pKa of the copolymer is lower than that of the copolymer without electron withdrawing groups.

23. The method of claim 1, wherein the adsorbing segment comprises amine groups so that the effective pKa of the copolymer is lower than that of the copolymer without amine groups.

* * * * *

UNITED STATES PATENT AND TRADEMARK OFFICE
CERTIFICATE OF CORRECTION

PATENT NO. : 7,029,688 B2 Page 1 of 1
APPLICATION NO. : 10/403344
DATED : April 18, 2006
INVENTOR(S) : Jeffrey A. Hubbell, Natalie D. Winblade and Donald L. Elbert It is certified that error appears in the above-identified patent and that said Letters Patent is hereby corrected as shown below:

Col. 12;
Claim 11, line 36, replace "add" with --acid--.

Signed and Sealed this

Fourth Day of September, 2007

JON W. DUDAS
*Director of the United States Patent and Trademark Office*